(12) United States Patent
Belrhlid et al.

(10) Patent No.: US 6,358,549 B2
(45) Date of Patent: *Mar. 19, 2002

(54) SULFUR CONTAINING FLAVORINGS

(75) Inventors: Rachid Belrhlid, Epalinges; Alain Chaintreau, Plan le Ouates; Philippe Pollien, Forel, all of (CH)

(73) Assignee: Nestec S.A., Vevey (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,313

(22) Filed: Apr. 29, 1999

(30) Foreign Application Priority Data

May 7, 1998 (EP) ............................. 98201490

(51) Int. Cl.$^7$ ............................. H23L 1/227
(52) U.S. Cl. ...................... 426/533; 426/534
(58) Field of Search ................. 426/534, 533

(56) References Cited

U.S. PATENT DOCUMENTS

| | | | |
|---|---|---|---|
| 3,394,015 A | 7/1968 | Giacino | 99/140 |
| 3,706,577 A | 12/1972 | Kats et al. | 99/140 |
| 4,076,852 A | 2/1978 | Van Delft et al. | 426/533 |
| 4,081,565 A | 3/1978 | Chhuy et al. | 426/533 |
| 4,161,550 A | 7/1979 | Bernhardt et al. | 426/533 |
| 4,218,487 A * | 8/1980 | Jaegi | 426/553 |
| 5,747,302 A * | 5/1998 | Huynh-Ba et al. | 435/117 |
| 5,948,453 A * | 9/1999 | Cerny et al. | 426/48 |

FOREIGN PATENT DOCUMENTS

| | | |
|---|---|---|
| AU | 71981/76 | 6/1997 |
| EP | 0 571 031 | 11/1993 |

OTHER PUBLICATIONS

Ashurst, P.R., Food Flavorings, Blackie Academic & Professional, Chapman & Hall, p. 283–293, 1991.*

Arctander, S. Perfume and Flavor Chemicals., I., 917, 1969.*

D.S. Mottram et al., Interaction of Thiol and Disulfide Compounds with Food Components, Journal of Agriculture and Food Chemistry, vol. 44, No. 8, 1996, pp. 2349–2351.

* cited by examiner

*Primary Examiner*—Arthur L. Corbin
(74) *Attorney, Agent, or Firm*—Winston & Strawn

(57) ABSTRACT

A precursor mixture of flavorings and a food composition containing the precursor mixture of flavorings. The precursor mixture of flavorings includes at least one polysulfide and at least one non-volatile source of sulfur having at lease one sulfhydryl group. The precursor mixture generates an aromatic note due to the formation of thiols when heated to provide a roasted or grilled flavor to the food composition.

12 Claims, 1 Drawing Sheet

SULFUR CONTAINING FLAVORINGS

TECHNICAL FIELD

The present invention relates to a precursor mixture of flavorings and flavoring components and to their use in the manufacture of food compositions.

BACKGROUND ART

It is known that sulfur-containing compounds are important constituents used to flavor foods. Indeed, it is disclosed, in the "BACIS, VFC96, database of volatile compounds in food, 1996" that thiol groups are present in food flavorings, and give off a roasted odor or a grilled odor when cooked. For example, the roasted odor or grilled odor is formed during the cooking of a variety of food compositions such as, meats, eggs, or vegetables; during the process of beer-making; and the roasting of coffee.

Unfortunately, thiols are unstable compounds which are often lost by evaporation or by oxidation. Hofmann et al. in J. Agric Food Chem., 1996, 44, 251–255 showed that thiols are oxidized to the corresponding disulfides after storage at a temperature of 60° C.

Mottram et al., in J. Agric Food Chem., 1996, 44, 2349–2351, maintain that thiol groups can be formed by the reaction, in a hot aqueous solution, of disulfide compounds with proteins having sulfhydryl groups, in particular cysteines, or disulfide bridges, in particular cystines. In particular Mottram et al. reveals that heating an aqueous solution containing a disulfide and albumin leads to the release of thiol groups in a yield of 44.8%. That article, however, is entirely theoretical and does not mention either the possibility of starting with natural products or the formation of a complex. Furthermore, there is no application to the manufacture of flavorings.

U.S. Pat. No. 3,706,577, FR 1,423,176, EP 571,031, FR 2,222,030 and FR 2,205,280 relate to processes for manufacturing ready-to-use flavorings. In these patents, the aim is to manufacture an overall flavoring, i.e., a non-specific flavoring.

Thus, there remains a need for flavorings which specifically promote the release of a grilled odor or of a roasted odor during the cooking or heating of food compositions, and the present invention resolves this need.

SUMMARY OF THE INVENTION

The present invention relates to a precursor mixture of flavorings that includes at least one polysulfide and at least one non-volatile source of sulfur having at least one sulfhydryl group. The precursor mixture generates an aromatic note when it is heated due to the formation of thiols. The polysulfide is present in an amount sufficient to generate a thiol when heated to provide a roasted or grilled aromatic note. The non-volatile source of sulfur includes at least one sulfhydryl group and is present in an amount sufficient to react with the polysulfide to form the thiol and release of the aromatic note when the precursor mixture is heated.

The polysulfide can have the general formula R—$(S)_n$—R' wherein R and R' are identical or different and represent hydrogen; straight chain, branched chain or cyclic hydrocarbon groups, which may also include, unsaturation, heteroatoms and/or other functional groups; and aromatic groups, which may include heteroatoms, and which may be substituted or unsubstituted on the aromatic ring; and wherein n is greater than or equal to 2. The polysulfide may be obtained by bioconversion of a cysteine-aldehyde conjugate using a baker's yeast.

The non-volatile source of sulfur, which may or may not be combined with other constituents, is selected from the group consisting of sulfur-containing amino acids, peptides containing at least one sulfur-containing amino acid, proteins containing at least one sulfur-containing amino acid, and protein hydrolysates containing at least one sulfur-containing amino acid.

In one embodiment the thiol is formed in a yield of 48–90%, when heated at neutral pH. In another embodiment the non-volatile source of sulfur is selected to be one or more proteins comprising at least one sulfur-containing amino acid and a hydrophobic pocket which forms a complex with the one or more polysulfides. This precursor mixture made of the complex can be dried so as to obtain a stable powder.

The invention also relates to a food composition that includes a food and a precursor mixture of flavorings. The precursor mixture of flavorings generates a roasted or grilled aromatic note when the food composition is heated. The precursor mixture of flavorings is preferably added in a proportion of about 0.07–0.50% by weight relative to the dry weight of the food composition.

DETAILED DESCRIPTION OF PREFERRED EMBODIMENTS

Figure 1:
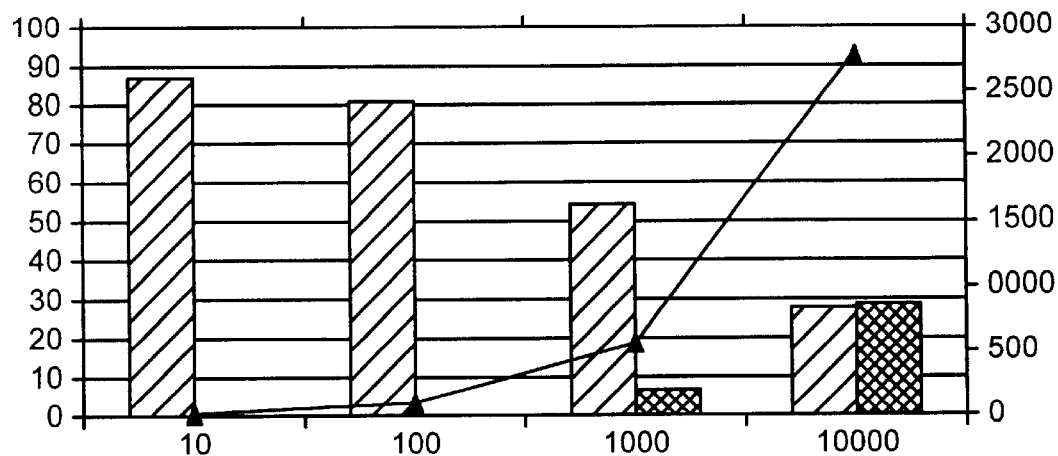
FIG. 1 is a plot showing the yield of thiol as a function of the amount of disulfide relative to the protein.

The present invention relates to a precursor mixture of flavorings which generates an aromatic note when heated due to the formation of thiols. Preferably, the precursor mixture of flavorings comprises a polysulfide and a non-volatile source of sulfur having at least one sulfhydryl group. The precursor mixture may be a complex which is formed between a polysulfide and a non-volatile source of sulfur having at least one sulfhydryl group. Formation of the complex has a protective effect on the polysulfide. According to the present invention the thiols are formed in situ, and thus, the phenomenon of thiol instability is minimized. Finally, natural thiols can be prepared from starting compounds which are also natural.

The present invention relies on the presence of one or more sulfhydryl groups which are reacted with one or more polysulfides, to allow the release of an aromatic note. By sulfhydryl group is meant the functional group —SH.

In the remainder of the description, the expression "aromatic note" or the term "odor" will be used indifferently to denote the formation of a flavoring which is perceptible in sensory terms, by means of the sense of smell or via the retronasal route.

Preferably, the polysulfide is of general formula R—$(S)_n$—R' in which R and R' are identical or different and n is greater than or equal to 2. R and R' can be hydrogens; straight chain, branched chain or cyclic hydrocarbon groups, which may also include, unsaturation, heteroatoms and/or other functional groups; or aromatic groups, which may include heteroatoms, and which may be substituted or unsubstituted on the aromatic ring. It is possible, for example, to use as the polysulfide, a dimethyl disulfide, a bis(2-furfuryl) disulfide, a bis-(3-methyl-2-furyl) disulfide, a bis (3-methyl-2-buten-1-yl) disulfide, or a thioketone disulfide, such as bis(2-oxopropyl) disulfide.

The polysulfide can be obtained by bioconversion of a cysteine-aldehyde conjugate using a baker's yeast in a phosphate buffer at pH 7–9, preferably at pH 8, containing 10-30 mM of cysteine-aldehyde conjugate.

The non-volatile source of sulfur, which may or may not be combined with other constituents, includes, but is not limited to sulfur-containing amino acids, peptides containing at least one sulfur-containing amino acid, proteins containing at least one sulfur-containing amino acid, and/or protein hydrolysates containing at least one sulfur-containing amino acid. Cysteine, glutathione, egg albumin, gluten, BSA, milk proteins or milk protein hydrolysates, for example, can be used as non-volatile source of sulfur.

By non-volatile source of sulfur is meant a sulfur compound that does not readily evaporate at normal temperature and pressure or that decomposes under heating (for example cysteine decomposes at 175° C.).

Preferably, the precursor mixture is heated at neutral pH, so as to allow the formation of thiols in a yield of 48–90%. The aromatic notes are not generated until the precursor mixture is heated above about 50° C., more preferably above about 75° C., and most preferably above about 100° C.

The precursor mixture of flavorings can be used in the manufacture food compositions, so as to promote the development of a roasted or grilled aromatic note when the food composition is heated in aqueous medium or under dry conditions. In particular, it is possible to use the precursor mixture in the manufacture of sauces; soups; refrigerated or frozen cooked meals; and freeze-dried food compositions, such as products based on soluble coffee. Preferably, the precursor mixture is added to the food composition in a proportion of about 0.07–0.50% relative to the dry weight of the food composition.

The food composition can be heated with microwaves or in a conventional oven and can be heated in aqueous medium, under dry conditions, or in boiling water, for example. The precursor mixture then releases a pronounced roasted odor or a pronounced grilled odor.

In one embodiment of the invention the precursor mixture of flavorings includes, as the non-volatile source of sulfur, one or more proteins containing at least one sulfur-containing amino acid, and having a hydrophobic pocket which interacts with the one or more polysulfides to form a complex, thus allowing the polysulfides to be protected from degradation. This complex can be dried so as to obtain the precursor mixture as a stable powder. The complex can be dried by spraying or by freeze-drying, for example.

EXAMPLES

The invention is further defined by reference to the following tests and examples described below. The tests and examples are representative and should not be construed to limit the scope of the invention in any way. In these tests and examples, the percentages are given in mole percent, except where otherwise indicated.

Test 1: Reaction between bis(2-furfuryl) disulfide and a protein source comprising at least one sulfhydryl group.

Bis(2-furfuryl) disulfide was reacted, in aqueous medium, under hot conditions (100° C.), with several protein sources, so as to produce 2-furfuryl thiol. The 2-furfuryl thiol was isolated using a machine for simultaneous distillation-extraction ("SDE"), at atmospheric pressure or under vacuum. The identity of the recovered furfuryl thiol (and for all the thiols generated in the other examples) was confirmed using gas chromatography-mass spectrography by comparing the retention time of the peak generated by the gas chromatograph and the mass spectrum of the recovered material to a reference sample of the thiol.

The yield for formation of thiol groups was determined by integrating the area of the peak obtained from gas chromatography analysis. Peak areas were calibrated using an internal standard. This yield of thiol is expressed as a percentage and is calculated on the basis of the amount of thiol groups which should be formed, i.e., twice the molar amount of disulfide. The data are given in Table 1.

TABLE 1

| | (a) | Protein source | Yield | Isolation method |
|---|---|---|---|---|
| Control | | | <1% | SDE/atmospheric pressure (100° C.) |
| Test No.1 | 10 ppm | Egg albumin | 87% | SDE/atmospheric pressure (100° C.) |
| Test No.2 | 10 ppm | Denatured egg albumin | 61% | SDE/atmospheric pressure (100° C.) |
| Test No.3 | 10 ppm | Egg albumin | <1% | SDE/under vacuum (37° C.) |
| Test No.4 | 100 ppm | Gluten | 45% | SDE/atmospheric pressure (100° C.) |
| Test No.5 | 100 ppm | BSA | 51% | 5DE/atmospheric pressure (100° C.) |
| Test No.6 | 100 ppm | β-lactoglobulin | 60% | SDE/atmospheric pressure (100° C.) |
| Test No.7 | 1000 ppm | β-lactoglobulin + 1% cysteine | 80% | SDE/atmospheric pressure (100° C.) |
| Test No.8 | 100 ppm | β-lactoglobulin hydrolysate | 20% | 5DE/atmospheric pressure (100° C.) |

Key: (a) amount of bis(2-furfuryl) disulfide/amount of protein source.

The results given in Table 1 reveal that the reaction, in aqueous medium under hot conditions (100° C.), between a polysulfide, such as bis(2-furfuryl) disulfide, and a protein source comprising at least one sulfhydryl group leads to the formation of the corresponding thiol, in an advantageous yield.

Furthermore, Test No. 3 reveals that if bis(2-furfuryl) disulfide is reacted with albumin under vacuum at room temperature, the corresponding thiol is not formed and the initial disulfide is not retrieved. Since the unreacted disulfide is normally recovered using SDE this confirms that the disulfide is complexed in the hydrophobic pocked formed by the protein. Thus, it is possible to avoid the loss of polysulfide by evaporation and to limit the dispersion of its odor before heating the food composition to which the precursor mixture has been added.

In order to increase the yield of thiol, it is also possible to form a ternary complex comprising a disulfide, cysteine, and a protein, as illustrated by comparing Test No. 6 and Test No. 7.

Test 2: Effect of the amount of polysulfide relative to the amount of protein source containing at least one sulfhydryl on reaction yield.

The reaction yield was calculated as a function of the amount of polysulfide relative to the amount of protein source containing at least one sulfhydryl group.

To do this, several reactions were carried out with varying amounts of bis(2-furfuryl) disulfide but a constant amount of egg albumin. All reaction were carried out in an aqueous medium under hot conditions (100° C.).

The yield for formation of thiol groups was then calculated. The yield is expressed as a molar percentage and is calculated on the basis of the amount of thiol groups which should be formed, i.e., twice the molar amount of disulfide.

The results are depicted in FIG. 1. In FIG. 1 the x-axis represents the amount of disulfide, in ppm, relative to the amount of protein. The left-hand y-axis represents the yield of thiol relative to the disulfide as a mole percent. The bar graphs having single diagonal lines represent the yield of thiol relative to disulfide in mole percent. The two bar graphs having cross-hatched diagonal lines, at disulfide concentrations of 1,000 and 10,000 ppm relative to the amount of protein, depict the amount of unconverted disulfide in mole percent. Finally, the triangles on the curve relate to the right-hand y-axis which represents the amount of thiol formed, in ppm, relative to the amount of protein.

FIG. 1 shows that the degree of conversion of the disulfide into furfuryl thiol decreases as the level of bis(2-furfuryl) disulfide complexed in the hydrophobic pocket of the protein increases. The bar graphs at disulfide concentrations of 1,000 and 10,000 ppm relative to the amount of protein show that a fraction of disulfide is not converted to thiol. The triangles show that the thiol content is nevertheless increased if the content of starting disulfide is increased.

Test 3: Reaction in an aqueous medium under hot conditions between egg albumin and different polysulfides in aqueous medium under hot conditions.

Egg albumin is reacted with different polysulfides, in an aqueous medium under hot conditions (100° C.). The yield for formation of thiol is calculated as described in Test 1. The results are given in Table 2.

TABLE 2

| | Polysulfide | (a) | Yield | Method of Isolation |
|---|---|---|---|---|
| Test No. 9 | Bis(2-furfuryl) disulfide | 10 ppm | 87% | SDE/atmospheric pressure |
| Test No. 10 | Bis(3-methyl-2-buten-1-yl) disulfide | 10 ppm | 30% | SDE/atmospheric pressure |
| Test No. 11 | 2-furfurylthiol | 100 ppm | 61% | SDE/atmospheric pressure |
| Test No. 12 | dimethyltrisulfide | 10 ppm | 7% | SDE/atmospheric pressure |

Key: (a) amount of polysulfide/amount of egg albumin

The results in Table 2 reveal that the reaction between a polysulfide and a protein source comprising at least one sulfhydryl group, in aqueous medium under hot conditions (100° C.), leads to the formation of the corresponding thiol.

Moreover, these results reveal the fact that the reaction between the polysulfide, bis(2-furfuryl) disulfide, and a protein source comprising at least one sulfhydryl group (Test No. 9) leads to the formation of the corresponding thiol in a better yield than in the case in which a simple complexation is carried out between the thiol group, 2-furfuryl thiol, and a protein source comprising a sulfhydryl group (Test No. 11). Without wishing to be bound by theory it is believed that this difference in yield is due to the fact that there is an irreversible reaction between the thiol group and the protein resulting in the formation of a disulfide bond between the protein and the thiol, to produce a compound that is not volatile, i.e., furfuryl-S-S-protein is formed when the thiol is 2-furfuryl thiol.

There is, however, no loss in yield of thiol from the reaction between a polysulfide and a protein source comprising at least one sulfhydryl group, since the corresponding thiol is released as soon as it is formed.

Test 4: Amino acids or peptides as the non-volatile source of sulfur comprising at least one sulfhydryl group.

Bis(2-furfuryl) disulfide and an amino acid or a peptide, as the non-volatile source of sulfur comprising at least one sulfhydryl group, were reacted together in an aqueous medium under hot conditions (100° C.). The ratio by mass of bis(2-furfuryl) disulfide/non-volatile source of sulfur comprising at least one sulfhydryl group was 1/10. The yield for formation of thiol is calculated as described in Test 1.

The results are given in Table 3.

TABLE 3

| | (b) | Yield | pH |
|---|---|---|---|
| Test No.13 | cysteine | 10–59% | — |
| Test No.14 | cysteine | 87% | 7.6 |
| Test No.15 | glutathione | 80% | 7.6 |
| Test No.16 | cystine | 2.8% | 7.6 |

Key: (b) non-volatile source of sulfur containing at least one sulfhydryl group or one disulfide bridge.

The results given in Table 3 reveal that when a precursor mixture of flavorings consisting of the volatile disulfide, bis(2-furfuryl) disulfide, and the sulfur-containing amino acid, cysteine, or the peptide containing at least one sulfur-containing amino acid, glutathione, is heated in an aqueous medium this leads to the formation of thiols, thus, generating an aromatic note.

In contrast, as illustrated by Test No. 16, if the non-volatile source of sulfur does not have a free sulfhydryl, such as cystine, which has a disulfide bridge, a negligible yield of thiol is obtained. The results given in Table 3 further reveal that the reaction is pH-dependent. If cysteine is reacted in distilled water, under hot conditions (100° C.), with bis(2-furfuryl) disulfide, as in Test No. 13, the yield of thiol ranges between 10 and 59%. On the other hand, if the same reaction is carried out in water at a pH of 7.6, as in Test No. 14, an 87% yield of thiol of is obtained.

Test 5: Formation of natural thiols.

The process is performed by the bioconversion of disulfides. The bioconversion is accomplished by suspending a baker's yeast in a phosphate buffer at pH 8 containing a cysteine-aldehyde conjugate at a concentration of about 20 mM. The bioconversion is carried out for 48 h. In order to compare the effect of oxygen on the formation of 2-furfuryl thiol half of the bioconversion is carried out in an anaerobic medium and the other half of the bioconversion is carried out in an aerobic medium. At various times the reaction yield is measured.

The optimum yield for formation of 2-furfuryl thiol was 30–40% in the anaerobic medium, and 10–25% in the aerobic medium. After incubation for 144 h, the optimum yield for the formation of bis(2-furfuryl) disulfide was 24% in the anaerobic medium and 4% in the aerobic medium.

Thus, natural bis(2-furfuryl) disulfide is prepared over 144 h under anaerobic conditions. The bis(2-furfuryl) disulfide was then reacted, in aqueous medium, under hot conditions (100° C.), with egg albumin, so as to produce 2-furfuryl thiol in a yield of 60%. The 2-furfuryl thiol was isolated using SDE, at atmospheric pressure.

Example 1

Soluble coffee was flavored using a precursor mixture of flavorings according to the invention, so as to develop a very pronounced grilled note. This was accomplished using a precursor mixture of flavorings, comprising 100 ppm of bis(2-furfuryl) disulfide and β-lactoglobulin. The mixture was reacted, under hot conditions (100° C.) in 100 ml of water at pH 7.5, containing 1.5 g of soluble coffee. The resulting mixture had a coffee taste with a very pronounced grilled note.

Example 2

A precursor mixture of flavorings in powdered form was prepared, which could readily be used to give a pronounced aromatic note to foods. The precursor mixture of flavorings in powdered form was prepared by mixing 100 ppm of bis(2-furfuryl) disulfide with albumin in water and freeze-drying the mixture. The resulting precursor mixture of flavorings in powdered form can readily be used dry, as a suspension, or as a solution, and in particular, can be heated with microwaves, such that it develops a very pronounced grilled aromatic note.

Example 3

A roast chicken liquid stock is prepared by adding a precursor mixture according to the invention thereto. A precursor mixture of flavorings as described in Example 2 was prepared and added to the stock in a proportion of 0.35% by weight relative to the dry weight of the stock. A roast chicken liquid stock was thus obtained with a very pronounced meat note.

Example 4

A hamburger was prepared by adding a precursor mixture according to the invention to the minced burger meat. A precursor mixture of flavorings as described in Example 2 was prepared and added to the burger in a proportion of 0.45% by weight relative to the dry weight of the minced burger meat. The burger thus prepared was placed on one half of a bread roll with a filling composed of lettuce, tomatoes and gherkins cut into rings, and the other half of the bread roll was placed on top. A hamburger having a very pronounced meat note when heated with microwaves was obtained.

What is claimed is:

1. A precursor mixture of flavorings consisting essentially of:
    at least one polysulfide that includes an -S-S bond, the polysulfide being present in a amount sufficient to generate a thiol when heated above 50° C. to provide a roasted or grilled aromatic note; and
    at least one non-volatile source of sulfur comprising at least one sulfhydryl group, wherein the non-volatile source of sulfur is present in an amount sufficient to react with the polysulfide to form the thiol and release the aromatic note when the precursor mixture is heated above 50° C.

2. A precursor mixture according to claim 1 in the form of a complex of the non-volatile source and the polysulfide.

3. A precursor mixture according to claim 1, wherein the polysulfide has the general formula R—$(S)_n$—R', wherein n is greater than or equal to 2 and R and R' are identical or different and represent hydrogen; straight chain, branched chain or cyclic hydrocarbon group, which optionally include, unsaturation, heteroatoms and/or other functional groups; or aromatic rings, which optionally include heteroatoms, and which optionally are substituted on, or incorporated in groups pendant to, the aromatic rings.

4. The precursor mixture of claim 3, wherein the polysulfide comprises at least one of dimethyl disulfide, bis(2-furfuryl) disulfide, bis(3-methyl-2-furyl) disulfide, bis(3-methyl-2-buten-1-yl) disulfide, or thioketone disulfide.

5. A precursor mixture according to claim 1, wherein the polysulfide is obtained by bioconversion of a cysteinealdehyde conjugate using baker's yeast.

6. A precursor mixture according to claim 1, wherein the non-volatile source of sulfur is selected from the group consisting of sulfur-containing amino acids, peptides containing at least one sulfur-containing amino acid, proteins containing at least one sulfur-containing amino acid, and protein hydrolysates containing at least one sulfur-containing amino acid.

7. A precursor mixture according to claim 1, wherein the thiol is formed in a yield of 48–90%, when heated above 50° C. at a neutral pH.

8. A precursor mixture according to claim 1, wherein the non-volatile source of sulfur is selected to be one or more proteins comprising at least one sulfur-containing amino acid and a hydrophobic pocket which forms a complex with the one or more polysulfides.

9. A precursor mixture according to claim 8, wherein the precursor mixture is dried so as to obtain a stable powder.

10. A flavoring agent comprising the precursor mixture of claim 1.

11. The flavoring agent of claim 10, included in a food product.

12. The flavoring agent of claim 11, wherein the mixture is present in an amount of about 0.07% to 0.50% by weight relative to the dry weight of the food product.

* * * * *

UNITED STATES PATENT AND TRADEMARK OFFICE
CERTIFICATE OF CORRECTION

PATENT NO.    : 6,358,549 B2
DATED         : March 19, 2002
INVENTOR(S)   : Belrhlid et al.

It is certified that error appears in the above-identified patent and that said Letters Patent is hereby corrected as shown below:

<u>Title page,</u>
Item [75], Inventors: change the city address of Alain Chaintreau from "Plan le Ouates" to -- Plan les Ouates --.

<u>Column 7,</u>
Line 34, change "an -S-S bond," to -- an -S-S- bond, --.

<u>Column 8,</u>
Line 7, change "hydrocarbon group, which optionally" to -- hydrocarbon groups, which optionally --.
Lines 17-18, change "of a cysteinealde-hyde conjugate" to -- of a cystein-aldehyde conjugate --.

Signed and Sealed this

Tenth Day of September, 2002

Attest:

JAMES E. ROGAN
*Attesting Officer*   *Director of the United States Patent and Trademark Office*